United States Patent [19]

Chorvat

[11] 4,348,328
[45] Sep. 7, 1982

[54] 25-SUBSTITUTED-5α-CHOLESTANE-3β,22S-DIOL

[75] Inventor: Robert J. Chorvat, Arlington Heights, Ill.

[73] Assignee: G.D. Searle & Co., Skokie, Ill.

[21] Appl. No.: 319,519

[22] Filed: Nov. 9, 1981

[51] Int. Cl.³ .............................................. C07J 9/00
[52] U.S. Cl. ............................................... 260/397.2
[58] Field of Search ..................................... 260/397.2

[56] References Cited

U.S. PATENT DOCUMENTS

| | | |
|---|---|---|
| 4,193,930 | 3/1980 | Chorvat ............................ 260/397.2 |
| 4,205,004 | 5/1980 | Chorvat ............................ 260/397.2 |
| 4,230,626 | 10/1980 | Chorvat ........................... 2 60/397.2 |
| 4,299,774 | 10/1981 | Chorvat ............................ 260/397.2 |

Primary Examiner—Elbert L. Roberts
Attorney, Agent, or Firm—James G. Passe´

[57] ABSTRACT

25-Substituted-5α-cholestane-3β,22S-diols and esters thereof of Formula I which inhibit the activity of 3-hydroxy-3-methyl-glutaryl coenzyme A reductase and inhibit the formation of serum cholesterol are disclosed.

9 Claims, No Drawings

25-SUBSTITUTED-5α-CHOLESTANE-3β,22S-DIOL

BACKGROUND OF THE INVENTION

This invention relates to certain novel cholestane derivatives. In particular, this invention relates to novel cholestane derivatives of formula I which are useful in that they inhibit the activity of 3-hydroxy-3-methylglutaryl coenzyme A reductase (HMGCOA) and inhibit the formation of serum cholesterol. HMGCOA is an enzyme which controls the rate at which cholesterol is synthesized in mammalian liver (one of the two principal in vivo sources of serum cholesterol). Thus, the compounds of the instant invention, are adapted to inhibit sterol biosynthesis in individuals predisposed to familial type II hypercholesterolemia. The significance of such compounds is widly recognized, eg, Breslow et al. Biochem. et Biophys. Acta, 398, 10 (1975); Betteridge et al., Brit. Med. J., 4 500 (1975); and Brown et al., J. Biol. Chem., 249, 7306 (1974).

SUMMARY OF THE INVENTION

The present invention particularly provides compounds of formula I:
wherein $R_1$ and $R_2$ are:
  (a) hydrogen; or
  (b) an esterifying moiety of the formula
  $HO-C(O)-(CH_2)_n-C(O)-$; $R_1$ and $R_2$ each being the same or different;
wherein n is an integer from 1 to 3;
wherein $R_3$ is:
  (a) halogen; or
  (b) alkyl of 1 to 6 carbon atoms inclusive.

Examples of alkyls of from one to six carbon atoms inclusive are methyl, ethyl, propyl, butyl, pentyl, and hexyl and the isomeric forms thereof, with methyl being preferred. Examples of halogen include fluorine, chlorine, and bromine. Examples of the esterifying moiety are 2-carboxyl-1-oxoethyl, 3-carboxyl-1-oxopropyl, and 4-carboxyl-1-oxobutyl.

The HMG CoA reductase-inhibitor activity of the instant compounds and their inhibition of the formation of serum cholesterol can be demonstrated via the following standardized test procedure: Male Charles River CD rats initially weighing 180–250 g apiece, are randomized in groups of 6, housed in a reverse light cycle (12:12) room, and maintained therein on a standard rat diet plus water ad libitum. To each animal in a group, after at least 3, but not more than 6 days, 5 mg/kg of 20,25-diazacholesterol dissolved in 0.2 ml of physiological saline containing 0.1 percent of polyoxyethylene sorbitan monooleate (Tween 80) is intragastrically administered on each of 7 consecutive days, during the last 4 of which the test compound is concurrently and identically administered at a pre-selected daily dose (commonly 5 mg/kg intragastrically). Controls are provided by a second group of animals identically treated except that test compound is omitted. Within 2–4 hr after treatment is completed, and 5–7 hr into the dark cycle, the animals are anesthetized with 1,1'-oxybisethane and thereupon killed. Livers are quickly removed, washed with a chilled homogenization medium (preparable by dissolving 102.7 g of sucrose, 3.8 g of sodium edetate, and 0.8 g of dithiothreitol in water q.s. 1000 ml), blotted dry, weighed, and homogenized (using 2 ml of the aforesaid chilled medium for each g of liver). The homogenates are centrifuged at 4° C. and 15,000×g for 15 min., whereupon the supernatants are separated and centrifuged at 4° C. and 100,000×g for 60 min. The resultant supernatants are discarded and the residues suspended in half the volume of homogenization medium previously employed (i.e., 1 ml for each g of residue). HMG CoA reductase activity is assayed substantially in accordance with procedures described by L. W. White et al. in Biochemistry, 9, 2713 (1970); M. S. Brown et al. in Biochim. Biophys. Acta, 409, 39 (1975).

Protein is determined by the method of O. H. Lowry et al., J. Biol. Chem., 193, 265 (1951). The data obtained are converted to specific activity (mmol/20 min./mg protein) for each animal, from which group mean(s) and percent change, relative to controls, are calculated. A statistically significant response ($P \geq 0.05$) is the criterion for HMG CoA reductase inhibition/stimulation.

For therapeutic purposes, the compounds of this invention are ordinarily combined with one or more adjuvants appropriate to the indicated route of administration. If per os, they may be admixed with lactose, sucrose, starch powder, cellulose esters of alkanoic acids, cellulose alkyl ethers, talc, stearic acid, magnesium stearate, magnesium oxide, sodium and calcium salts of phosphoric and sulfuric acids, gelatin, acacia, sodium alginate, polyvinylpyrrolidone, and/or polyvinyl alcohol, and thus tableted or encapsulated for convenient administration; alternatively, they may be dissolved or suspended in water or a comparably innocuous liquid. Parenteral administration may be effected via sterile fluid admixture with water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art: see, for example, F. W. Martin et al., "Remington's Pharmaceutical Sciences", 14 Ed., Merck Publishing Company, Eaton, Pa., 1965.

Appropriate dosages, in any given instance, of course, depend upon the nature and severity of the condition treated, the route of administration, and the species of mammal involved, including its size and any individual idiosyncrasies which obtain.

The compounds of the invention may be made in accordance with the scheme on Charts A and B. The precursors may be made in accordance with the methods outlined in either U.S. Pat. No. 4,230,621 or U.S. application Ser. No. 06/278,276 which is hereby incorporated by reference using the appropriate known starting materials. Cholene derivatives of formula II where $R_3$ is F, alkyl or hydroxy are hydrogenated to yield the dihydroxy compound of formula III. The dihydroxy compound may then be esterified by the methods described in the above references. Where $R_3$ is chlorine or bromine, the cholene derivative is hydrogenated prior to incorporation of the halogen as in the site protected alcohol of formula XI. The site protected compound is then hydrogenated to yield the formula XII compound and chlorine or bromine then incorporated at the 25 position (formula XIII). This compound may be deacetylated with lithium aluminum hydride and THF to form the dihydroxy compound of formula XIV, which then in turn may be converted in to the esterified compound XV.

DESCRIPTION OF THE PREFERRED EMBODIMENTS

The operation of this invention is further elaborated by the representative examples below:

EXAMPLE 1

25-methyl-5α-cholestane-3β,22-diol 25-methylcholest-5-en-3β-22-diol and 0.3 gm of 10 percent Palladum/Carbon is heated for 25 hours at 60° C., in isopropyl alcohol (150 ml) under a Hydrogen atmosphere at 60 psi. The solvent is removed in vacuo to give about 0.6 gm of a white solid which is recrystallized from an ethyl acetate/methanol then methanol and finally an ethyl acetate/Skelly B solvent system to give the pure title compound which has a melting point of 195°–196° C. Elemental analysis for the compound is: calculated, hydrogen: 12.04, carbon: 80.32; found, hydrogen: 11.82, carbon: 80.39.

EXAMPLE 2

25-methyl-5α-cholestane-3β,22-diol 3-hydrogen butanedioate 200 mg of the title compound of Example 1 and 0.1 gm of succinic anhydride in 3 ml of pyridine is heated on a steam bath for 24 hours. Water is then added along with 1 N HCl and the percipitate which forms is collected (250 mg). The percipitate is recrystallized from aqueous methanol to give upon cooling 155 mg of the title compound, having a melting point of 194°–198° C. Elemental analysis for the compound is: calculated, hydrogen: 10.49, Carbon: 74.09; found, hydrogen: 10.51, carbon: 74.28.

EXAMPLE 3

Cholestan-3β,22,25 triol,3,22-diacetate 1.0 g of 3,22-diacetoxy-25-hydroxy cholesterol and 6.2 g of Platinum/O$_2$ in 30 ml isopropyl alcohol is heated for 18 hours at 60° C. in a hydrogen atmosphere at 60 psi; the solution is then filtered and the filtrate is then concentrated in vacuo to give 0.98 gm of a white solid, the title compound.

EXAMPLE 4

25-chloro-cholestane-3β,22S-diol, diacetate 2.6 g of the product of Example 3, 1.2 g of zinc chloride, 4 ml of thionyl chloride, and 180 ml of toluene is stirred at room temperature for one-half hour. The mixture is then washed with 5 percent sodium carbonate solution then water, dried over magnesium sulfate and filtered. The filtrate is concentrated in vacuo to give an oily residue which is recrystallized from methanol to give 1.85 g of a white crystalline solid, the title compound.

EXAMPLE 5

25-fluoro-5α-cholestane-3β,22S-diol 25-fluorocholest-5-ene-3β,22-diol and 0.25 mg of 10 percent Palladium/carbon in 150 ml of isopropyl alcohol is heated at 60° C. for 24 hours in a hydrogen atmosphere at 60 psi. The reaction mixture is filtered to remove the catalyst and the solvent removed in vacuo to give 0.5 g of a white solid. The solid is recrystallized from aqueous methanol to give the pure title compound as the hydrate, having a melting point of 174° C. to 176° C. Elemental analysis for the compound is: calculated, hydrogen: 11.21, carbon: 73.59; found, hydrogen: 11.02, carbon: 73.29.

EXAMPLE 6

25-chloro-5α-cholestane-3β,22S-diol

In a 100 ml flask equipped with a magnetic stirrer and a nitrogen atmosphere, is placed 300 mg lithium aluminum hydride suspended in 15 ml of THF. 1.8 grams of 25-chlorocholestane-3β,22-diol,3-acetate is taken up in 15 ml of THF and is added under a nitrogen atmosphere over a period of 10 min. The mixture of the above is stirred at room temperature for 1 hour, then treated with 1.5 ml of water and is stirred at room temperature for 2 hr. The mixture is then filtered and the filtrate is concentrated on a steam bath to dryness to afford a semi-solid residue which is crystallized twice from methanol to afford the title compound as a white solid having a melting point of 165°–167° C. Elemental analysis for the compound is: calculated, hydrogen: 10.79, Carbon: 73.85; found, hydrogen: 10.84, carbon: 73.79.

EXAMPLE 7

25-methylcholestane-3β,22-diol bis (hydrogen butanedioate)

To 4 parts of 25-methylcholest-5-en-3β,22-diol,3 hydrogen butanedioate is added 40 parts of pyridine, 2 parts of succinic anhydride and 1.4 parts of 4-dimethylaminopyridine, and the reaction mixture heated at about 90° C. for six hours. The cooled reaction mixture is poured into a 5 percent HCl solution and this solution is extracted three times with ethyl acetate. The combined extracts are washed with saturated sodium chloride solution and dried over magnesium sulfate. The dried solution is then treated with activated charcoal and filtered. Solvent removed gives a solid residue which, upon recrystallization from aqueous methanol, affords the pure title compound.

EXAMPLE 8

25-chloro-5α-cholestane-3β,22-diol bis (hydrogen butanedioate)

Using appropriate starting material and the methods described above the title compound may be prepared.

CHART A

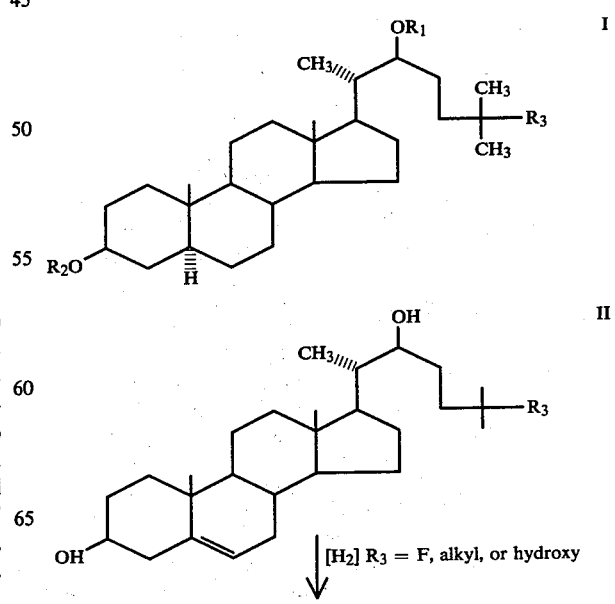

-continued
CHART A

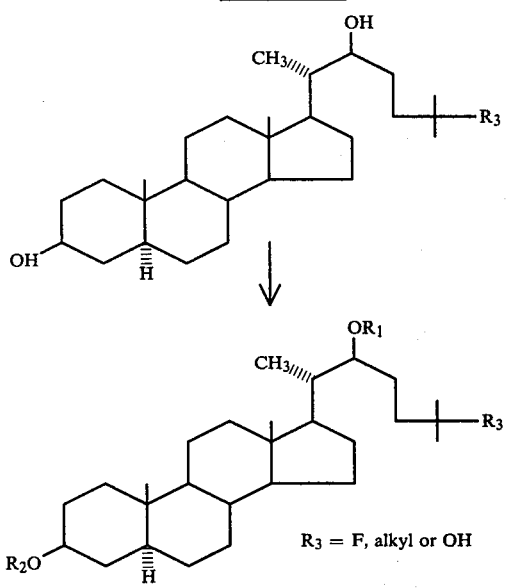

$R_3$ = F, alkyl or OH

CHART B

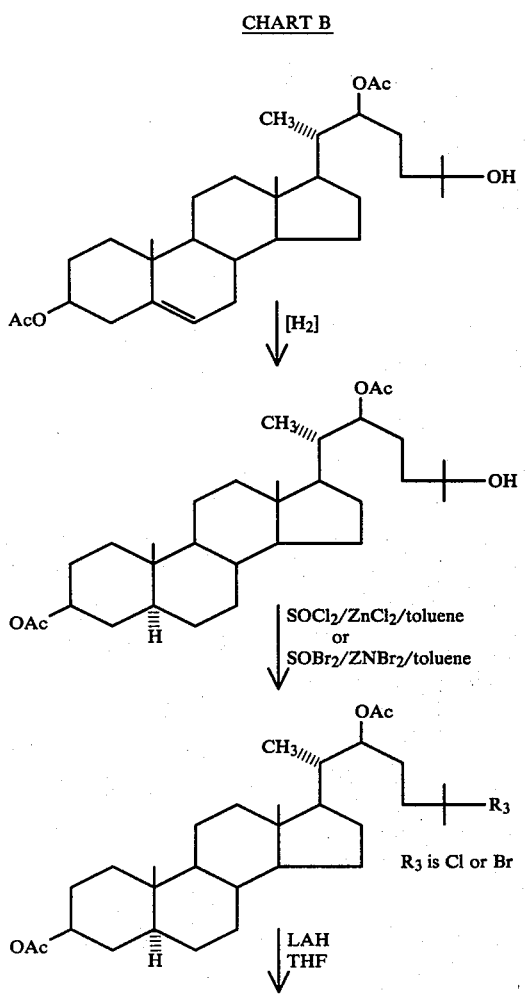

-continued
CHART B

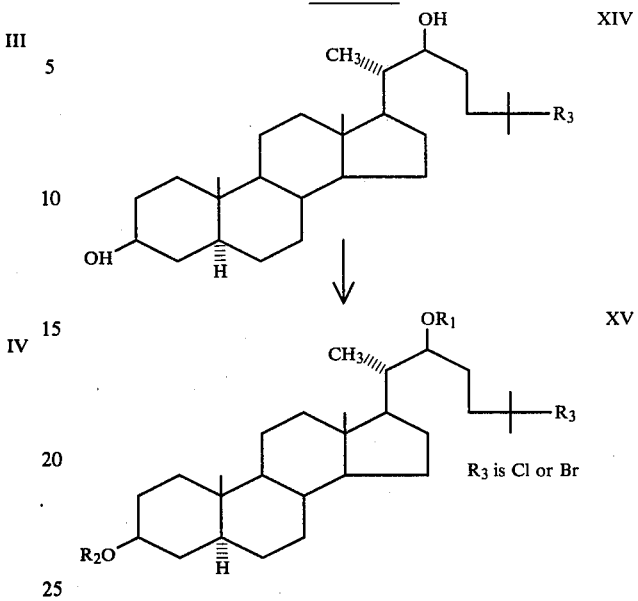

What I claim is:
1. A compound of the formula:

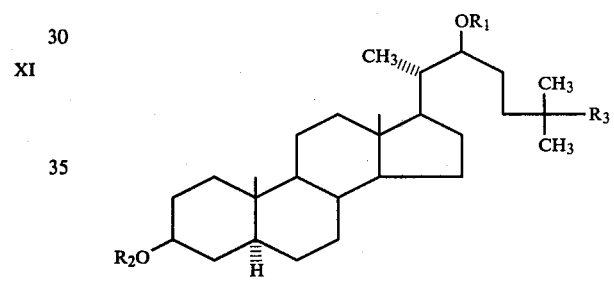

wherein $R_1$ and $R_2$ are:
(a) hydrogen; and
(b) an esterifying moiety of the formula HO—C(O)—(CH$_2$)$_n$—C(O)—; $R_1$ and $R_2$ each being the same or different;
wherein n is an integer from 1 to 3;
wherein $R_3$ is:
(a) halogen
(b) alkyl of 1 to 6 carbon atoms inclusive.
2. A compound according to claim 1 wherein $R_3$ is halogen.
3. 25-fluoro-5α-cholestane-3β,22S-diol, a compound according to claim 2.
4. 25-chloro-5α-cholestane-3β,22S-diol, a compound according to claim 2.
5. 25-chloro-5α-cholestane-3β,22-diol bis (hydrogen butanedioate), a compound according to claim 2.
6. A compound according to claim 1 wherein $R_3$ is alkyl of 1 to 6 carbon atoms.
7. 25-methyl-5α-cholestane-3β,22-diol, a compound according to claim 6.
8. 25-methyl-5α-cholestane-3β,22-diol-3-hydrogen butanedioate, a compound according to claim 6.
9. 25-methyl-5α-cholestane-3β,22-diol bis (hydrogen butanedioate), a compound according to claim 6.

* * * * *